United States Patent [19]

Vedamuthu

[11] Patent Number: 4,874,616
[45] Date of Patent: Oct. 17, 1989

[54] METHOD FOR PRODUCING MUCOID AND PHAGE RESISTANT GROUP N STREPTOCOCCUS STRAINS FROM NON-MUCOID AND PHAGE SENSITIVE PARENT STRAINS

[75] Inventor: Ebenezer R. Vedamuthu, Bradenton, Fla.

[73] Assignee: Microlife Technics, Inc., Sarasota, Fla.

[21] Appl. No.: 188,469

[22] Filed: Apr. 29, 1988

Related U.S. Application Data

[62] Division of Ser. No. 786,631, Oct. 11, 1985.

[51] Int. Cl.⁴ .................... A23C 9/12; A23C 19/00; C12N 15/00
[52] U.S. Cl. ................................. 426/43; 426/330.2; 426/334; 426/583; 435/170; 435/172.3; 435/252.3; 435/253.4; 435/320
[58] Field of Search ............. 426/43, 330.2, 334, 426/34, 583; 435/170, 172.3, 252.3, 320, 885, 253.4; 935/22, 29, 59, 60, 72

[56] References Cited

U.S. PATENT DOCUMENTS 4,382,097 5/1983 Vedamuthu .................. 426/43

OTHER PUBLICATIONS

Hammer, B. W., Iowa Agr. Expt. Sta. Research Bul., 74:260–270, (1923).
Foster, E. M. et al., Dairy Microbiology, pp. 14–15, 48 and 332, (1957).
Rasic, J. L. et al., Yoghurt-Scientific Grounds, Technology, Manufacture and Preparations, p. 194, (1978).
Bottazzi, V., Biotechnology, vol. 5, pp. 328, 345–346, (1983).
Macura, D. et al., J. Dairy Sci., 67:735–744, (1984).
Saxelin, M. et al., Canadian J. Microbiol., 25:1182–1187, (1979).
Forsen, R., Finnish J. Dairy Sci., 20:1, (1966).
Brooker, B. E., J. Dairy Research, 43:283–290, (1976).
Botazzi, V., Other Fermented Dairy Products, pp. 328, 345–346, In G. Reed (ed.), Biotechnology-Bol. 5, Food and Feed Production with Microorganisms.
Verlag Chemie, Weinheim, Fed. Rep. of Germany, (1983).
McKay et al., Applied Environmental Microbiology, 47:68–74, (1984).
Sozzi et al., Milchwissenschaft, 33:349–352, (1978).
McKay, L. L., (Antonie van Leeuwenboek), J. Microbiol, 49:259–274, (1983).
Klaenhammer, T. R., Advances in Applied Microbiology, 30:1–29, (1984).
Gonzalez, C. F. et al., Appl. Environ. Microbiol., 46:81–89, (1983).
McKay, L. L. et al., Appl. Environ. Microbiol., 40:84–91, (1980).
Niven, C. F. et al., J. Bacteriol., 43:651–660, (1942).
King, N., Dairy Industries, 13:860, (1948).
Anderson, D. G. et al., Appl. Environ. Microbiol., 46:549–552, (1983).
McKay, L. L., Regulation on Lactose Metabolism In Dairy Streptococci, p. 153–182.
In: R. Davis (ed.), Dev. In Food Microbiology-1. Applied Science Pub. Ltd., Essex, England, (1982).
Gasson, M. J., (Antonie van Leeuwenhoek), J. Microbiol., 49:275–282, (1983).
Walsh, P. M. et al., J. Bacteriol., 146:937–944, (1981).
Langeveld, L. P. H., Neth Milk Dairy J., 29:135, (1975).

Primary Examiner—Thomas G. Wiseman
Assistant Examiner—Richard C. Peet
Attorney, Agent, or Firm—Ian C. McLeod

[57] ABSTRACT

A method for imparting phage resistance to phage sensitive strains of *Streptococcus* group N is described. The method involves transferring plasmid encoding for production of a mucoid substance (Muc+) into the phage sensitive strain. Even if the Muc+ plasmid is removed by curing at elevated temperatures the strains remain resistant to phage. The resulting resistant strains are novel and are used for fermentations, particularly milk fermentations.

3 Claims, 3 Drawing Sheets

METHOD FOR PRODUCING MUCOID AND PHAGE RESISTANT GROUP N STREPTOCOCCUS STRAINS FROM NON-MUCOID AND PHAGE SENSITIVE PARENT STRAINS

This is a divisional of copending application Ser. No. 786,631, filed on Oct. 11, 1985.

BACKGROUND OF THE INVENTION (1) Field of the Invention

The present invention relates to a method for producing phage resistant bacteria from phage sensitive strains of Streptococcus in N group of this genus. Further the present invention relates to novel bacterial compositions including phage resistant strains of Streptococcus in N group of this genus derived from phage sensitive strains.

(2) Prior Art

The occurrence of lactic streptococci that produce a mucoid, ropy texture in milk is well documented (Hammer, B. W., Iowa Agr. Expt. Sta. Research Bul. 74:260–270 (1923)). Such ropy lactic streptococci are used in Scandinavian fermented milks called taette (Foster, E. M., et al., Dairy Microbiology, p. 14–15, 48 and 332, (1957); Rasic, J. L. et al., Yoghurt-Scientific grounds, technology, manufacture and preparations, p. 194 (1978)), Swedish lang mjolk (Bottazzi, V., Biotechnology, Vol. 5, p. 328, 345–346 (1983); Macura, D., et al., J. Dairy Sci. 67:735–744 (1984)) and Finnish villii (Saxelin, M., et al., Canadian J. Microbiol. 25:1182–1187 (1979)). Forsen, R., Finnish J. Dairy Sci. 26:1 (1966) isolated mucoid strains of all three lactic streptococci, namely, *Streptococcus cremoris*, *Streptococcus lactis* and *Streptococcus lactis* subsp. *diacetylactis*, from Finnish villii.

The instability of mucoid characteristic in lactic streptococci has been observed by several investigators (Foster, E. M., et al., Dairy Microbiology. p. 14–15, 48 and 332 (1957); Hammer, B. W., Iowa Agr. Expt. Sta. Research Bul. 74:260–270 (1923); and Macura, D., et al. J. Dairy Sci. 67:735–744 (1984)). Foster et al reported that mucoid lactic streptococci gained or lost the slime-producing property "capriciously". Macura and Townsley found that ropy lactic streptococci lost the mucoid property after 10 or 12 serial transfers; some strains became non-mucoid even after six transfers. Brooker (Brooker, B. E., J. Dairy Research 43:283–290 (1976)) working with a pure milk culture of a ropy *S. cremoris* strain observed considerable variations in the proportion of cells producing extracellular capsular material. Traditionally, in the production of Scandinavian ropy milks, low temperature incubation between 13° C. to 18° C. is preferred, because incubation at temperatures higher than 27° C. to 30° C. resulted in considerable reduction or loss of desirable high viscosity and mucoidness (Bottazzi, V., Other Fermented Dairy Products. p. 328, 345–346. In: G. Reed (ed.), Biotechnology-Vol. 5, Food and Feed Production with Microorganisms, Verlag Chemie, Weinheim, Federal Republic of Germany (1983); and Macura, D., et al. J. Dairy Sci. 67:735–744 (1984)). It had been suggested by early prior art that the mucoidness might protect the lactic Streptococcus against bacteriophage; however, this was shown to be wrong. Sozzi et al, Milchwissenschaft 33, 349–352 (1978).

The association of several metabolic functions in lactic streptococci with plasmid DNA is now well recognized (McKay, L. L., J. Microbiol. 49:259–274 (1983)). On the basis of the observed instability of ropy characteristic in lactic streptococci, Macura and Townsley (Macura, D., et al., J. Dairy Sci. 67:735–744 (1984)) and McKay suggested that plasmid DNA may be involved in the expression of mucoid phenotype (Muc+).

A problem in the prior art is to be able to produce phage resistant strains of Streptococcus which are members of the N group. It would be highly desirable to be able to impart phage resistance to strains of Streptococcus which are phage sensitive since these bacteria are very important in commercial fermentations for producing fermented milk products. McKay et al, Applied Environmental Microbiology, 47; 68–74 (1984) describes limited phage resistance which is plasmid associated. Klaenhammer, J., Advances in Applied Microbiology 30, 1–29 (1984) at page 22 discusses plasmid encoded phage resistance. Phage resistance has not been associated with a 18.5 Mdal plasmid in *Streptococcus cremoris* encoding for mucoidness. Further, *Streptococcus cremoris* NRRL-B-15995 was obtained as a single colony isolated from a phage resistant strain but is a slow acid producer and thus is not a useful strain for milk fermentations.

OBJECTS

It is therefore an object of the present invention to provide a method for imparting phage resistance to Streptococcus of the N group which are phage sensitive. Further it is an object of the present invention to provide novel phage resistant bacteria derived from phage sensitive strains. These and other objects will become increasingly apparent by reference to the following description and the drawings.

IN THE DRAWINGS

GENERAL DESCRIPTION

Figure 1:
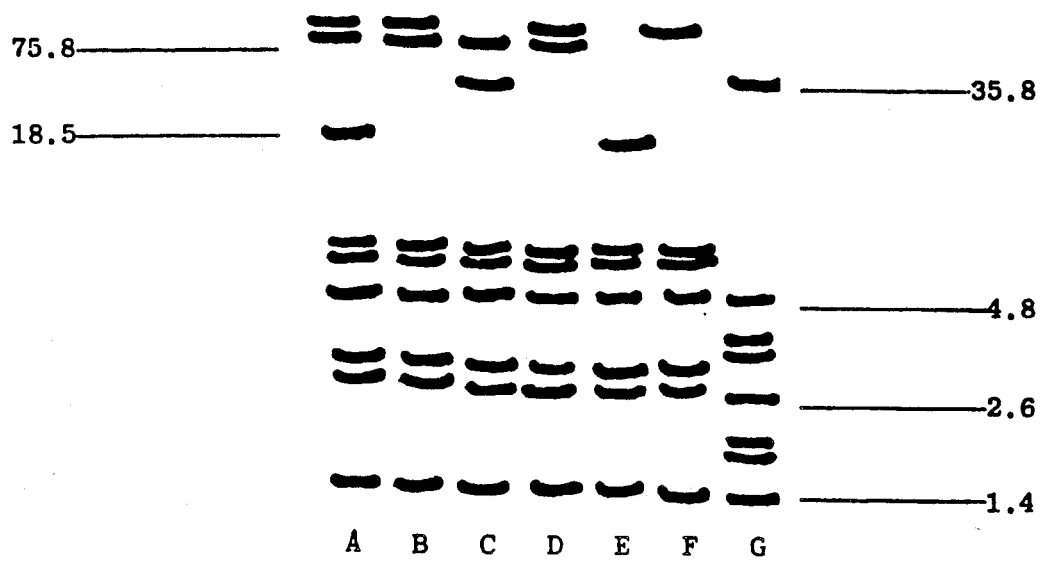
FIG. 1 is a drawing of an agarose gel electrophoreis of plasmid DNA from *Streptococcus cremoris* MS and its cured derivatives showing an 18.5 Mdal plasmid which encodes for mucoid substance production. These are as follows: (A) Parent strain MS (B) MS01 (c) MS02 (D) MS03 (E) MS04 (F) MS05 and (G) Reference plasmid DNA for molecular sizing from Eschericia coli V517.

The present invention relates to a method for imparting phage resistance to Streptococcus bacteria which comprises: providing a phage sensitive bacteria of the genus Sreptococcus group N which is lysed by a homologous phage; and introducing a transferred plasmid into the phage sensitive bacteria to thereby produce a phage resistant bacteria which is resistant to the homologous phage, wherein the transferred plasmid contains DNA derived from a parental plasmid which encodes for a mucoid substance around the outside of *Streptococcus cremoris* (MS) NRRL-B-15995.

Further the present invention relates to a phage resistant bacteria of the species *Streptococcus lactis* or *Streptococcus lactis* subspecies *diacetylactis* in substantially pure form derived from a phage sensitive bacteria and containing plasmid DNA derived from a parental plasmid which encodes for a mucoid substance from *Streptococcus cremoris* (MS) NRRL-B-15995, wherein the phage resistant bacteria is reistant to a homologous phage, and to heat cured phage resistant derivatives of the phage resistant bacteria with the plasmid integrated into bacteria so as to be unidentifiable, generally into the chromosomes of the bacteria.

The present invention also relates to a phage resistant bacteria of the species *Streptococcus lactis* or *Streptococcus lactis* subspecies *diacetylactis* which were derived from phage sensitive parent cells by conjugal transfer of a plasmid which encodes for a mucoid substance in *Streptococcus cremoris* (MS) NRRL-B-15995. Further, the present invention relates to heat cured Muc⁻ derivatives of the phage resistant transconjugants lacking the 18.5 Mdal plasmid which still retain resistance to homologous phages.

The bacterial cells can be prepared for use as a concentrate having a pH between about 4 and 8 and containing at least about $1 \times 10^7$ cells per gram up to about $10^{15}$ cells per gram, usually between about $1 \times 10^9$ and $10^{12}$ cells per gram. The concentrates can be frozen with or without a freezing stabilizing agent such as monosodium glutamate, malt extract, non-fat dry milk, alkali metal glycerophosphate, glutamic acid, cystine, glycerol, or dextran or the like and then thawed for use or the concentrates can be lyophilized or dried by other means to a powder as is well known to those skilled in the art. The bacterial cells are generally used in a range between about $10^5$ to $10^9$ cells per ml of milk to be fermented, depending upon the product to be produced. All of this is very well known to those skilled in the art. U.S. Pat. No. 3,429,742 describes various preservation methods.

U.S. Pat. No. 4,382,097 to one of the inventors herein describes mixed cultures including mucoid substance producing (Muc+) strains. The phage resistant, mucoid substance producing strains of the present invention can be used in the preparation of these mixed cultures with good results.

SPECIFIC DESCRIPTION

The following Example shows the involvement of plasmid DNA (Muc plasmid) in the expression of the Muc+ phenotype in *Streptococcus cremoris* MS. Additionally, the Example shows the conjugal transfer of Muc-plasmid from a ropy *Streptococcus cremoris* to a non-mucoid (Muc⁻) *Streptococcus lactis* and from the resultant mucoid *Streptococcus lactis* transconjugant to a malty variant of *Streptococcus lactis* (formerly *Streptococcus lactis* var. *maltigenes*) and a strain of *Streptococcus lactis* subsp. *diacetylactis* and the expression of Muc+ phenotype in all the transconjugants. The resultant transconjugant *Streptococcus lactis* and *Streptococccus lactis* subsp. *diacetylactis* strains are phage resistant. The phage susceptibility of the malty *Streptococcus lactis* transconjugant was not determined because of the unavailability of a lytic phage for the parent strain. It is believed to be phage resistant.

*Streptococcus cremoris* MS (NRRL-B-15995) when grown in milk at 24° C., ferments lactose (Lac+) and produces a mucoid (ropy) coagulum (Muc+). *Streptococcus cremoris* MS was isolated by the inventor from milk products and it is not available from any other source. By incubating *Streptococcus cremoris* MS at 38° C., several non-mucoid (Muc⁻) isolates were obtained. Comparison of plasmid profiles of mucoid and non-mucoid isolates showed that a 18.5 Mdalton plasmid (pSRQ2202) was involved in the expression of mucoid phenotype. Additionally, the curing experiments revealed that in *Streptococcus cremoris* MS, a 75.8 Mdalton plasmid (pSRQ2201) was associated with the ability to ferment lactose. Derivatives lacking pSRQ2201 did not ferment lactose (Lac⁻). In mating experiments using *Streptococcus cremoris* MS as donor, pSRQ2201 was conjugatively transferred to Lac⁻ *Streptococcus lactis* ML-3/2.2. The transconjugant *Streptococcus lactis* ML-3/2.201 was Lac+, which confirmed that pSRQ2201 coded for lactose utilization.

By indirect selection techniques using genetic markers for lactose utilization or phage resistance, pSRQ2202 was first conjugatively transferred from a Lac⁻, Muc+ derivative of Streptococcus cremoris MS (Strain MS04) to Lac+, Muc⁻ *Streptococcus lactis* ML-3/2.201. The resultant transconjugant *Streptococcus lactis* ML-3/2.202 was Lac+ and Muc+. Subsequently, pSRQ2202 was co-mobilized with pSRQ2201 in mating experiments, from *Streptococcus lactis* ML-3/2.202 (NRRL-B-15996) (donor) to a plasmid-free, Lac⁻, Muc⁻ malty *Streptococcus lactis* 4/4.2, and a Lac⁻, Muc⁻ *Streptococcus lactis* subsp. *diacetylactis* SLA3.25. The respective transconjugants were Lac+ and Muc+ confirming that pSRQ2201 and pSRQ2202 encoded for Lac+ and Muc+ phenotypes respectively. With the transfer of pSRQ2202, the transconjugants *Streptococcus lactis* ML-3/2.202 (NRRL-B-15996) and *Streptococcus lactis* subsp. *diacetylactis* SLA3.2501 (NRRL-B-15994) and 18-16.01 (NRRL-B-15997 not only acquired Muc+ phenotype but also resistance to phages, which were lytic to respective parent strains, namely *Streptococcus lactis* ML-3/2.201 and *Streptococcus lactis* subsp. *diacetylactis* SLA3.25 and 18-16. The strains marked with an NRRL number were deposited with the Northern Regional Research Laboratory, Peoria, Ill. and are freely available to those who request them by name and number.

Example 1

MATERIALS AND METHODS

Cultures and Phages: Bacterial strains used in this study are listed in Table 1.

TABLE 1

| Streptococcus Strain | Chromosomal Phenotype[a] | Plasmid (Mdal) | Description or Source[a,b] |
|---|---|---|---|
| *S. cremoris* | | | |
| MS | None | 105.6, 75.8, 35.8, 18.5, 6.3, 5.8, 4.7, 3.0, 2.7, 1.5. | Wild type; this study; Lac+Muc+ |
| MS01 | None | 105.6, 75.8, 6.3, 5.8, 4.7, | Lac+Muc⁻ |

TABLE 1-continued

Bacterial Strains

| Streptococcus Strain | Chromosomal Phenotype[a] | Plasmid (Mdal) | Description or Source[a,b] |
|---|---|---|---|
| MS02 | None | 3.0, 2.7, 1.5<br>105.6, 75.8, 35.8, 6.3, 5.8<br>4.7, 3.9, 2.7, 1.5 | Lac$^+$Muc$^-$ |
| MS03 | None | 105.6, 75.8, 18.5, 6.3, 5.8<br>4.7, 3.0, 2.7, 1.5 | Lac$^+$Muc$^+$ |
| MS04 | None | 105.6, 18.5, 6.3, 5.8, 4.7,<br>3.0, 2.7, 1.5 | Lac$^-$Muc$^+$ |
| MS0401 | None | 105.6, 75.8, 18.5, 6.3, 5.8,<br>4.7, 3.0, 2.7, 1.5. | MS04 transconjugant<br>Lac$^+$Muc$^+$ |
| MS05 | None | 105.6, 6.3, 5.8, 4.7, 3.0,<br>2.7, 1.5 | Lac$^-$Muc$^-$ |
| MS05.2 | Sm$^r$Fus$^r$ | 105.6, 6.3, 5.8, 4.7, 3.0,<br>2.7, 1.5 | Lac$^-$Muc$^-$Sm$^r$Fus$^r$ |
| TR | None | Not determined | Lac$^+$Muc$^-$<br>Commercial strain |
| TR01 | None | Not determined | Lac$^+$Muc$^+$<br>Transconjugant<br>(ML-3/2.202.1 × TR) |
| S. lactis | | | |
| SLA 1.1 | Sm$^r$ | None | Sm$^r$, LMO230 |
| SLA 1.8 | Rif$^r$ | None | Rif$^r$, LMO230 |
| ML-3/2.2 | Sm$^r$ Fus$^r$ | 5.2, 2.2, 1.5 | Lac$^-$ ML-3, Sm$^r$,<br>Fus$^r$ |
| ML-3/2.201 | Sm$^r$ Fus$^r$ | 75.8, 5.8, 5.2,<br>2.2, 1.5 | Lac$^+$ transconjugant of<br>ML-3/2.2 |
| ML-3/2.202 | Sm$^r$ Fus$^r$ | 75.8, 18.5, 5.8,<br>5.2, 2.2, 1.5 | Lac$^+$ Muc$^+$<br>transconjugant<br>of ML-3/2.201 |
| ML-3/2.202.1 | Sm$^r$ Fus$^r$ | 18.5, 5.8, 5.2<br>2.2, 1.5 | Lac$^-$Muc$^+$<br>ML-3/2.202 |
| Malty 4/4.2 | Rif$^r$ Fus$^r$ | None | Rif$^r$ Fus$^r$ plasmid<br>cured derivative<br>of malty S.<br>lactis 4 |
| Malty 4/4.201 | Rif$^r$ Fus$^r$ | 75.8, 18.5, 5.8 | Transconjugant of<br>malty 4/4.2;<br>Lac$^+$ Muc$^+$ |
| S. lactis subsp. diacetilactis | | | |
| 18-16 | None | 41, 28, 6.4,<br>5.5, 3.4, 3.0 | Lac$^+$Muc$^-$<br>Commercial Strain |
| SLA 3.25 | Rif$^r$ | 25.8, 5.5, 4.7, 3.4, 3.2 | Lac$^-$ Rif$^r$<br>derivative of<br>strain 18-16 |
| SLA 3.2501 | Rif$^r$ | 75.8, 25.8, 18.5, 5.8<br>5.5, 4.7, 3.4, 3.2 | Transconjugant of<br>SLA3.25; Lac$^+$<br>Muc$^+$ |
| 18-16.01 | None | 61, 28, 25<br>5.5, 3.4, 3.0 | Lac$^+$Muc$^+$<br>Transconjugant<br>(ML-3/2.202.1 x<br>18-16 |

[a]Fus - Fusicid acid; Rif - Rifampin; Sm - Streptomycin; r - resistant
[b]Lac$^+$- lactose fermenting; Lac$^-$ - lactose negative; Muc$^+$ - mucoid; Muc$^-$ - non-mucoid Phage c2 lyses *Streptococcus lactis* C$_2$ and *Streptococcus lactis* ML-3. Phage 643 is lytic for *Streptococcus lactis* ML-3 and lytic phage (designated phage 18-16) plaques on *Streptococcus lactis* subsp. *diacetylactis* 18-16 and SLA 3.25.

Culture Media and Propagation: Cultures that fermented lactose (Lac$^+$) were routinely propagated in sterile 10% reconstituted non-fat dry milk (NFM) at 24° C. for 14–16 hours. Strains that were lactose negative (Lac$^-$) were grown in sterile NFM fortified with 0.5% glucose and 0.2% yeast extract (FNFM).

Stock cultures grown in NFM or FNFM containing 10% sterile glycerol as cryoprotectant were dispensed into cryogenic vials and stored in liquid nitrogen. For routine use, additional vials of cultures were stored in a freezer held at −60° C.

In curing experiments to eliminate Muc$^+$ phenotype either NFM or FNFM was initially used. Later, BMG broth (Gonzalez, C. F., et al., Appl. Environ. Microbiol. 46:81–89 (1983)) was used, and for the selection and purification of Lac$^-$ colonies, BML agar (BMLA) described by Gonzalez and Kunka was used. Milk-indicator agar (MIA) was used for the selection and purification of phenotypes expressing variations of Lac and Muc (Lac$^\pm$ Muc$^\pm$) in curing and mating experiments. MIA was made up in two separate parts which after sterilization and tempering at 60° C. were mixed together. The first part consisted of distilled water at half the final volume of the medium (final volume 1 liter), containing the required amount of non-fat milk solids to give a final concentration of 5%; the second part consisted of the remaining half of distilled water containing the required amount of agar to obtain 1.5% in the final medium, and 10.0 ml of 0.8% aqueous solution of bromocresol purple.

Donor and recipient cultures for mating were grown to logarithmic phase (6–8 hours at 24° C.) in either whey broth (Lac+ strains) or whey-glucosse broth (Lac− strains). Whey broth (WB) was made in two parts, sterilized separately and after cooling, mixed together. To make up 1 liter of WB, 70.0 g of sweet whey powder (Pallio Dairy Products Corp., Campbell, N.Y.) was dissolved in 500 ml distilled water and centrifuged to remove undissolved residue. To the clear supernatant, 19.0 g sodium-beta-glycero phosphate (Sigma Chemical Co., St. Louis, Mo.) was added, mixed well and sterilized at 121° C. for 15 minutes. The second portion of the medium consisted of 5.0 g yeast extract, 10.0 g tryptone, 5.0 g gelatin, 0.5 g sodium acetate, 0.5 g $MgSO_4.7H_2O$ and 0.2 g $CaCl_2.2H_2O$ dissolved in 500 ml distilled water. After sterilization at 121° C. for 15 minutes the two parts were mixed together when cooled (at 50° C.). Whey-glucose broth (WBG) was made up by including 5.0 g of glucose in the formulation for WB. Matings were performed on 5% milk-glucose agar (MGA) plates as described by McKay et al (McKay, L. L., et al., Appl. Environ. Microbiol. 40:84–91 (1980)).

Curing: For temperature curing, S. cremois strains were incubated between 38° C. and 39° C.; Streptococcus lactis and Streptococcus lactis subsp. diacetylactis strains were incubated between 41° C. and 42° C. For eliminating Lac+ phenotype, cultures inoculated at the rate of 0.05% in BMG were incubated overnight at elevated temperatures and plated at suitable dilutions onto BMLA plates. Presumptive white Lac− colonies were confirmed for inability to ferment lactose and purified by single colony isolation on BMLA. For eliminating Muc+ phenotype, cultures inoculated at 0.05% in NFM/FNFM or BMG were incubated at elevated temperatures overnight and suitable dilution plated on MIA plates. Individual colonies were picked either into NFM (Lac+) or FNFM (Lac−) and incubated at 24° C. until coagulation or thickening of milk occurred. The cultures were then tested for mucoidness with 1.0 ml graduated serological pipets. Resistance to easy flow and formation of stringiness (long ropy strands) during free fall from pipet tip were used as test criteria to establish mucoidness.

Mating: In each mating experiment, two donor: recipient ratios (i.e. 1:2 and 1:4) were used. Mating mixtures and respective donor and recipient controls spread on MGA plates were incubated overnight at 24° C. in a Gas Pak anaerobic jar (BBL Microbiology Systems, Cockeysville, Md.). Cells from the surface of MGA plates were harvested with sterile Basal broth (BM, Gonzalez and Kunka set forth previously), using 1.0 ml BM per plate. Washings from each set of plates containing one experimental variable (i.e., plates with donor cells or recipient cells or mating mixture 1:2 or mating mixture 1:4) were pooled together, centrifuged and resuspended in 1.0 ml BM. The entire suspension was then plated onto five BMLA plates (0.2 ml per plate) containing appropriate concentration of selective drugs. Streptomycin (Sm) was added to obtain a final concentration of 1000 micrograms per ml; fusidic acid (Fus) to a final concentration of 20 micrograms per ml and Rifampin (Rif) to a final concentration of 300 micrograms per ml. Plates were incubated at 24° C. for 72 hours and examined. All Lac+ colonies were transferred to NFM to test for mucoidness. Mucoid isolates were purified by single colony isolation on MIA and subjected to confirmatory tests.

In mating experiments where specific lytic phage was used as selective agent, pelleted cells harvested from MGA plates were resuspended in 2.0 ml of high titer phage lysate ($>10^7$ PFU/ml). One-tenth ml of 0.2 M $CaCl_2$ was added to each tube, mixed gently and allowed to stand for 15 to 20 minutes at room temperature for phage adsorption. The contents of each tube were then spread on 10 BMLA plates (0.2 ml per plate).

For donor input counts, dilutions were plated on BMLA (Lac+) or BMGA (Lac−). Platings for counts were made immediately before mating mixtures and controls were spread on MGA. Transfer frequencies were calculated as the number of mucoid colonies per donor colony-forming-unit (CFU). Mating experiments were repeated at least once, and in some cases twice. To exclude transduction as a possible mode of genetic transfer, in parallel mating mixtures, donor culture aliquots were replaced with an equal amount of cell-free filtrates (Millipore filter, 0.45 micron-pore size, Millipore Corp. Bedford, Mass.) of the donor. To exclude transformation, DNAse at a final concentration of 100 micrograms per ml was added to the mating mixture prior to plating and to the MGA used. As a negative control to show that live cells are needed for the observed genetic transfer, in parallel mating mixtures, donor culture aliquots were replaced with heat-killed (boiling water-bath for 10 minutes) donor culture portions.

Confirmatory Tests: Confirmatory testing was done for arginine hydrolysis (Niven, C. F., Jr., et al., J. Bacteriol. 43:651–660 (1942)), diacetyl-acetoin production from citrate in milk (King, N., Dairy Industries 13:800 (1948)), and susceptibility to specific phages by spot test on seeded agar-overlay plates. Where necessary resistance or sensitivity to additional drug markers not selected for in the mating protocols was determined.

Cell lysis and Electrophoresis: For rapid screening of strains for plasmids, the method described by Anderson and McKay (Anderson, D. G., et al. Appl. Environ. Microbiol. 46:549–552 (1983)) was used. Procedures described by Gonzalez and Kunka (set forth previously) were used for routine examination of plasmid DNA, and for preparing purified plasmid DNA using cesium chloride gradients.

EXPERIMENTAL PROCEDURES

Curing of Muc+ Phenotype: Initial experiments with Streptococcus cremoris MS showed that mucoidness (or ropiness) in this strain could be easily eliminated by incubating inoculated NFM tubes at 38° C. for 14 to 16 hours. In three separate trials, an average of 30% of colonies isolated from MIA plates spread with Streptococcus cremoris MS which had been incubated at elevated temperatures in NFM, were non-mucoid. Twenty mucoid and 20 non-mucoid milk coagulating (in 18 to 24 hours at 24° C.) isolates were purified and examined for plasmid DNA content by agarose gel electrophoresis. All mucoid types with one exception, namely strain MS03, showed plasmid profiles similar to that of the wild type mucoid Streptococcus cremoris MS (FIG. 1). In Streptococcus cremoris MS03 the 35.8 Mdalton plasmid was absent. All the non-mucoid isolates with one exception showed plasmid profiles similar to Streptococcus cremoris MS01 (FIG. 1). In these strains, two plasmids, namely the 35.8 Mdalton and 18.5 Mdalton plasmids were missing. In the single non-mucoid isolate, Streptococcus cremoris MS02, only the 18.5 Mdalton plasmid was absent (FIG. 1). By examining the plasmid profiles of *Streptococcus cremoris* strains MS, MS01, MS02 and MS03, only the 18.5 Mdalton plasmid (pSRQ2202) could possibly be associated with MUC+ phenotype because strain MS03 retained the Muc+ phenotype even with the loss of 35.8 Mdalton plasmid. On the other hand, strain MS02, which possessed the larger 35.8 Mdalton plasmid became non-mucoid with the elimination of pSRQ2202.

Curing of Lac+ Phenotype: It is now well established that lactose fermenting ability in lactic streptococci is plasmid borne (McKay, L. L., Regulation of lactose metabolism in dairy streptococci, p. 153–182. In: R. Davis (ed.), Developments in Food Microbiology —1. Applied Science Publishers Ltd., Essex, England (1982)). To determine if Lac-plasmid in Muc+ *Streptococcus cremoris* MS03 could be cured without the loss of mucoid or ropy characteristic, the culture was incubated at 38° C. for 16 hours and plated on BMLA. Of a total of 80 colonies appearing on the BMLA plates, 15% were Lac−. All the Lac− colonies were transferred into the FNFM, incubated at 24° C. until thickening or coagulation occurred. The cultures were checked for mucoidness at that stage. With the exception of two isolates, all others were non-mucoid. *Streptococcus cremoris* MS04 represents the Lac− Muc+ phenotype (FIG. 1). Analysis of the plasmid profiles of Lac-cured derivatives suggested that the loss of lactose fermenting ability was associated with the elimination of 75.8 Mdalton plasmid (pSRQ2201). The Lac− Muc− phenotype is represented by *Streptococcus cremoris* MS05.

Development of Strategies for Transfer of Muc-plasmid: Alongside curing experiments, mucoid and non-mucoid strains were extensively examined for differences in carbohydrate fermentation patterns, resistance to different levels of NaCl, bile salts, ethanol, nisin and antioxidants like butylated hydroxyanisole (BHA) and butylated hydroxytoluene (BHT). No differences were observed that could be used to rapidly screen for mucoid types in the presence of non-mucoid types on agar plates. Further experiments in agar media containing various dyes and varous levels and combinations of sugar, milk components and minerals ($Mg^{++}$, $Ca^{++}$, $Mn^{++}$, $Fe^{+++}$) did not yield a good differential medium for visual distinction of mucoid from non-mucoid colonies. It was then decided to attempt indirect selection for possible mucoid types in genetic experiments. Because conjugative transfer of plasmids in lactic streptococci is well documented (Gasson, M. J., J. Microbiol. 49:275–282 (1983)), we decided to examine if Lac-plasmid in mucoid strains could be used as a metabolic marker to detect co-mobilization of Muc-plasmid in mating experiments.

Conjugative Transfer of Lac-plasmid: Several attempts to transfer Lac+ phenotype from *Streptococcus cremoris* MS (Lac+ Muc+ Sm$^s$; superscript s denotes "sensitive" throughout the text) to *Streptococcus cremoris* MS05.2 (Lac− Muc− Fus$^r$ Sm$^r$) and to the plasmid-free *Streptococcus lactis* SLA 1.1 (Lac− Muc− Sm$^r$) proved unsuccessful. In a later mating experiment, Lac+ phenotype was transferred from *Streptococcus cremoris* MS to *Streptococcus lactis* ML-3/2.2 (Lac− Muc− Sm$^r$ Fus$^r$). The transconjugant *Streptococcus lactis* M-3/2.201 was Lac+ but Muc− and had acquired a 75.8 Mdalton plasmid from *Streptococcus cremoris* MS. Additionally, the transconjugant was positive for arginine hydrolysis test and susceptible to phages c2 and 643. The expression of Lac+ phenotype by *Streptococcus lactis* ML-3/2.201 as a result of the acquisition of 75.8 Mdalton plasmid, pSRQ2201 from the donor, and the curing data obtained with *Streptococcus cremoris* MS and its derivatives indicated that pSRQ 2201 coded for lactose utilization in *Streptococcus cremoris* MS. Results from three independent mating experiments reconfirmed the association of Lac+ phenotype in transconjugants to the acquisition of pSRQ2201 from *Streptococcus cremoris* MS. Some of the transconjugants obtained in these matings exhibited clumping in broth cultures similar to the phenomenon previously reported by Walsh and McKay (Walsh, P. M., et al., J. Bacteriol. 146:937–944 (1981)). Parallel control experiments conducted with one of the matings to exclude transformation and transduction and negative control experiment using heat-killed donor *Streptococcus cremoris* MS cells showed that the transfer of Lac-plasmid was by conjugation.

Conjugative Transfer of Lac- and Muc-plasmids: A clumping Lac+ transconjugant *Streptococcus lactis* ML-3/2.201 was used as donor in a mating with *Streptococcus cremoris* MS04 to determine if the Lac-plasmid pSRQ2201 observed in the transconjugant *Streptococcus lactis* ML-3/2.201 could be transferred back to *Streptococcus cremoris* MS04, a Lac− Muc+ derivative of the wild type. The selective agent for this mating was phage c2 (at a titer of $1 \times 10^4$ PFU/ml) which lyses the donor, *Streptococcus lactis* ML-3/2.201. The phage does not infect the recipient *Streptococcus cremoris* MS04. Because of the low titer of phage used for selecting against donor cells, control donor plates showed several Lac+ survivor colonies per plate. Plates containing the mating mixtures, however, had at least twice as many Lac+ colonies per plate as the control donor plates. All acid-producing colonies from BMLA plates containing the mating mixtures were transferred into NFM and after incubation, checked for mucoidness. Randomly chosen 200 non-mucoid isolates were purified and checked for resistance to streptomycin (1000 micrograms per ml) on BMLA. All were resistant; additionally, they gave positive tests for liberation of $NH_3$ from arginine indicating that they were donor types. Six isolates that were mucoid were purified on MIA and checked for streptomycin sensitivity or resistance, and for arginine hydrolysis. Two of the mucoid isolates were negative for arginine hydrolysis and the other four were positive. Repurified isolates of the six mucoid cultures showed the same arginine hydrolysis characteristics as in the first testing. The two mucoid isolates that failed to liberate $NH_3$ from arginine were also sensitive to streptomycin (1000 micrograms per ml) and fusidic acid (20 micrograms per ml) indicating that they were recipient type Lac+ transconjugants. The remaining four mucoid cultures that were positive for arginine hydrolysis were resistant to the same levels of streptomycin and fusidic acid as the donor, *Streptococcus lactis* M-3/2.201. All six mucoid isolates were resistant to phages c2 and 643. Agarose gel electrophoresis of plasmid DNA from the six isolated showed that two types of transconjugants were obtained. The two arginine-negative, streptomycin sensitive Lac+ Muc+ isolates were recipient *Streptococcus cremoris* MS04 types that had acquired the Lac-plasmid (and Lac+ phenotype) from the donor (exemplified by *Streptococcus cremoris* MS0401, FIG. 2). The four arginine-positive, Lac+ Muc+ isolates were donor *Streptococcus lactis* M-3/2.202-type transconjugants that had acquired the 18.5 Mdalton Muc-plasmid from *Streptococcus cremoris*

Figure 2:
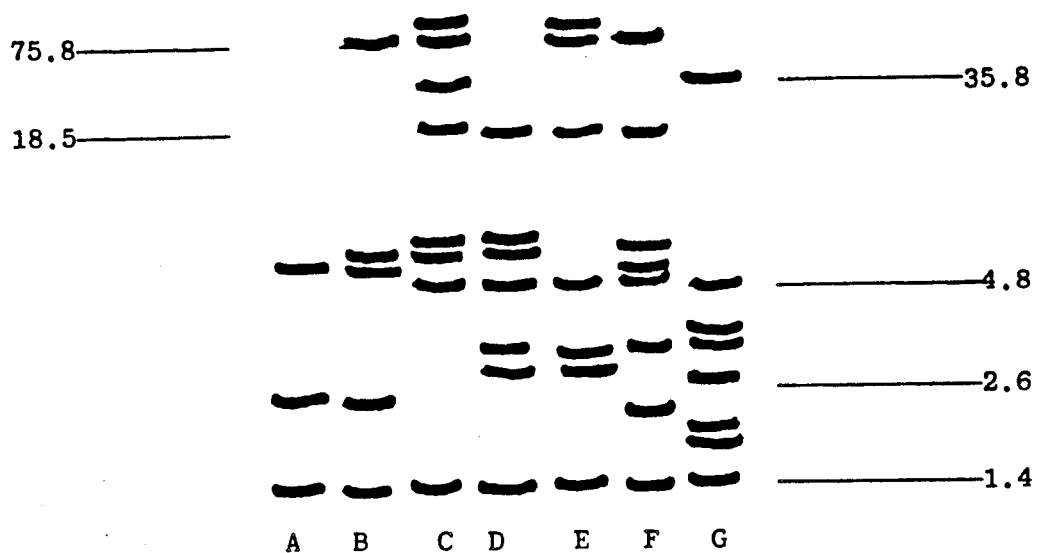
FIG. 2 is a drawing of an agarose gel electrophoresis of plasmid DNA from (A) *S. lactis* ML-3/2.2 (B) *S. lactis* ML-3/2.201 (C) *S. cremois* MS (D) *S. cremois* MS04 (E) *S. cremois* MS0401 (F) *S. lactis* ML-3/2.202 and (G) reference plasmid DNA for molecular sizing from *E. coli* V517.

MS04 (exemplified by *Streptococcus lactis* M-3/2.202, FIG. 2). Phage resistance of Muc+ transconjugants of donor *Streptococcus lactis* M-3/2.201 type suggested that the acquisition of 18.8 Mdalton plasmid pSRQ2202 and Muc+ phenotype conferred virus resistance to the ML-3/2.202 transconjugant, although the parent strain M-3/2.201 (Lac+ Muc−) was susceptible to the same phage. Based on these initial observations, the mating was repeated with *Streptococcus cremoris* MS04 as the donor and using a high titer c2 phage lysate ($3.0 \times 10^9$ PFU per ml) to select effectively against Lac+, phage-sensitive recipient *Streptococcus lactis* M-3/2.201 cells. Colony-free recipient control plates were obtained. Because the use of high titer phage lysate provided effective selection against non-mucoid, Lac+, phage-sensitive recipient cells, Lac+ colonies appearing on mating plates probably were transconjugants of donor *Streptococcus cremoris* MS04 type that had acquired the Lac-plasmid from *Streptococcus lactis* M-3/2.201 or were Muc+, phage-resistant transconjugants of M-3/2.201 type that had acquired the Muc-plasmid from *Streptococcus cremoris* MS04. Based on that premise, all Lac+ colonies from BMLA plates containing the mating mixtures were transferred into NFM and tested for mucoidness. All mucoid isolates were purified and subjected to confirmatory arginine hydrolysis test. With the use of high titer phage lysate transfer of Muc+ phenotype was observed at a frequency of $3.0 \times 10^{-4}$. Parallel control experiments conducted to exclude transformation and transduction and negative control experiment using heat-killed donor *Streptococcus cremoris* MS04 cells showed that the mode of transfer of Muc-plasmid from donor to recipient was conjugative.

Incubation of the Lac+ Muc+ transconjugant *Streptococcus lactis* ML-3/2.202 at 41° to 42° C. allowed the selection of all possible combinations of Lac± Muc± phenotypes. Agarose gel electrophoretic profiles of plasmid DNA from such derivatives confirmed that Lac+ phenotype was expressed when the 75.8 Mdalton pSRQ2201 plasmid was present and in the absence of that plasmid the bacteria were Lac−. Similarly, the presence and absence of 18.5 Mdalton pSRQ2202 plasmid was directly associated with the expression of Muc+ and Muc− phenotypes, respectively.

To further characterize the 18.5 Mdalton Muc-plasmid it was necessary to obtain the specific covalently closed circular DNA in a purified form. To obtain pSRQ2202 isolated by itself in parental or transconjugant strains, it would be necessary to cure several other resident plasmids in those strains. Alternatively, the Muc-plasmid could be transferred to a plasmid-free strain singly or in association with another plasmid—for example, Lac-plasmid—which then could be cured out leaving only the Muc-plasmid. *Streptococcus lactis* LM0230 and its plasmid-free derivatives have been successfully used as recipients for facilitating such transfer of desired plasmid singly or in association with another plasmid which could be cured out subsequently leaving only the desired plasmid in the recipient (McKay, L. L. et al., Appl. Environ. Microbiol. 47:68–74 (1984)). Accordingly, a mating experiment was conducted with *Streptococcus cremoris* 0401 (Lac+ Muc+ transconjugant) as the donor and *Streptococcus lactis* SLA 1.1 (plasmid-free Lac− Muc− Sm$^r$) as the recipient. Selection for transconjugants was based on Lac+ phenotype and streptomycin resistance. *Streptococcus cremoris* 0401 was chosen as the donor because it would allow analysis for an unselected marker (arginine hydrolysis) in presumptive transconjugant colonies. The MS0401×SLA 1.1 mating resulted in the transfer of Lac+ phenotype at a frequency of $2.0 \times 10^{-3}$; however, there was no transfer of Muc+ phenotype. Rapid screening of 200 Lac+ purified isolates from the mating plates that were arginine positive for plasmid DNA profiles revealed that in the majority of the isolates, in addition to the Lac-plasmid some of the resident cryptic plasmids in *Streptococcus cremoris* MS0401 were co-transferred. Attempts to co-transfer Muc-plasmid with the Lac-plasmid from *Streptococcus lactis* M-3/2.202 to plasmid-free *Streptococcus lactis* SLA 1.8 (Lac− Muc− Rif$^r$) proved unsuccessful.

Figure 3:
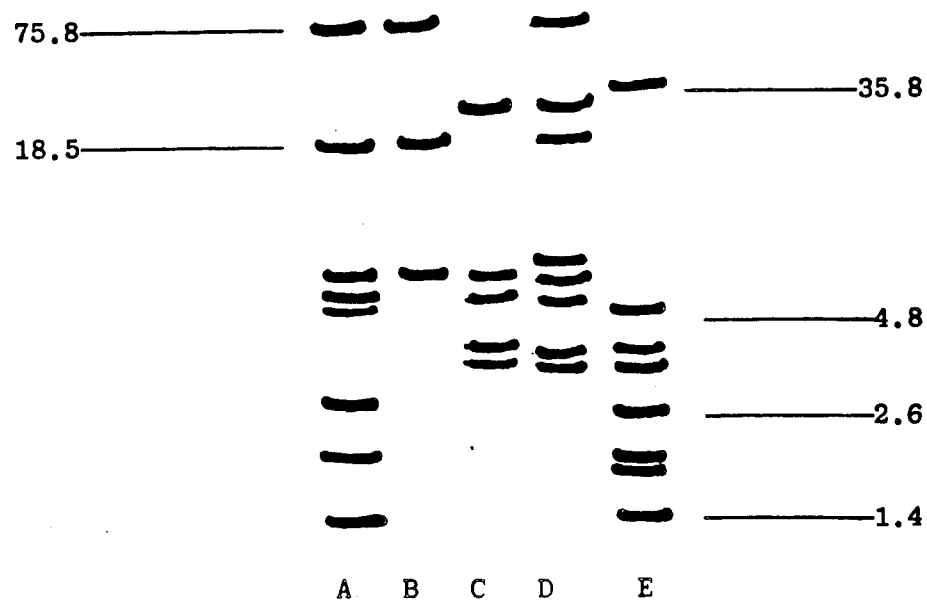
FIG. 3 is a drawing of an agarose gel electrophoresis of plasmid DNA from (A) *S. lactis* ML-3/2.202 (B) Malty *S. lactis* 4/4.201 (C) *S. lactis* subsp. *diacetylactis* SLA3.25 (D) *S. lactis* subsp. *diacetylactis* SLA3.2501 and (E) Reference plasmid DNA for molecular sizing from *E. coli* V517.

Co-transfer of Muc-plasmid with Lac-plasmid: As an alternative to *Streptococcus lactis* LM0230 derivatives, a plasmid-free, malty *Streptococcus lactis* 4/4.2 (obtained by curing two resident plasmids from the wild type malty strain *Streptococcus lactis* 4) was used as recipient in a mating with *Streptococcus lactis* M-3/2.202. Malty *Streptococcus lactis* 4/4.2 had Rif$^r$ and Fus$^r$ markers. The wild type malty *Streptococcus lactis* 4 gave a strong Lac+ reaction on BMLA and coagulated milk in 10 to 12 hours at 24° C. The plasmid-free, malty derivative *Streptococcus lactis* 4/4.2 exhibited a weak Lac+ reaction BMLA when incubated longer than 48 hours at 24° C. and failed to coagulate milk after 48 hours at 24° C. The indicator response in BMLA to threshold level of lactose utilization by *Streptococcus lactis* 4/4.2 was eclipsed by the addition of 0.5% disodium beta-gycerophosphate to BMLA. Plating of the mating mixtures on the buffered medium containing the selective antibiotic allowed the selection of Lac+ transconjugants. Lactose positive purified isolates screened for sensitivity to streptomycin were tested for Muc+ phenotype. Presumptive Lac+ Muc+ transconjugants were confirmed by testing for production of malty odor in milk containing sodium salt of 4 methyl-2 oxopentanoic acid (Langeveld, L. P. H. Neth. Milk Dairy J. 29:135 (1975)). Mobilization of other cryptic plasmids in addition to Muc-plasmid was observed with the transfer of Lac-plasmid from *Streptococcus lactis* M-3/2.202 to *Streptococcus lactis* 4/4.2 (FIG. 3). In repeat experiments with suitable controls, transfer of Lac- and Muc-plasmids was established to be conjugative. It was of interest to determine if Muc-plasmid could be co-transferred with Lac-plasmid to the third member of the lactic Streptococcus group; i.e., *Streptococcus lactis* subsp. *diacetylactis*. Mating experiments using *Streptococcus lactis* ML-3/2.202 as the donor and *Streptococcus lactis* subsp. *diacetylactis* SLA3.25 as the recipient were conducted. These matings yielded co-transfer of Lac- and Muc-plasmids to *Streptococcus lactis* subsp. *diacetylactis*; and, in some cases, transfer of only the Lac-plasmid was observed. The recipient *Streptococcus lactis* subsp. *diacetylactis* SLA3.25 and the Lac+ transconjugants were sensitive to phage 18-16. The Lac+ Muc+ transconjugant *Streptococcus lactis* subsp. *diacetylactis* SLA3.2501, however, was resistant to phage 18-16. By incubating the Lac+ Muc+ transconjugant SLA3.2501 at 41° to 42° C., all possible combinations of Lac and Muc phenotypes (Lac± Muc±) were obtained. As observed with *Streptococcus lactis* ML-3/2.202, the elimination of pSRQ2201 and pSRQ2202 from SLA3.2501 correlated with the inability of the derivatives to express Lac+ and Muc+ phenotypes respectively. In repeat experiments with suitable controls, co-transfer of Lac- and Muc-plasmids from *Streptococcus lactis* ML- 3/2.202 to *Streptococcus lactis* subsp. *diacetylactis* SA3.25 was confirmed to be conjugative.

Table 2 summarizes inter-species transfer frequencies for pSRQ2201 and pSRQ2202 singly and for the co-transfer of pSRQ2202 with the lac-plasmid from *Streptococcus lactis* ML-3/2.202 to malty *Streptococcus lactis* 4/4.2 and *Streptococcus lactis* subsp. *diacetylactis* SLA3.25.

TABLE 2

Frequency of inter-species transfer of plasmids pSRQ2201 and pSRQ2202 among lactic streptococci.[a]

| Plasmid | D × R[b,c] | | Transfer Frequency | Transconjugant[c] |
|---|---|---|---|---|
| pSRQ2201 | ScMS | S1 ML-3/2.2 | $7.01 \times 10^{-8}$ | S1 ML-3/2.201 |
| | S1 ML-3/2.201 | Sc MS04 | $0.3 \times 10^{-8}$ | Sc MS0401 |
| | Sc MS0401 | S1 SLA1.1 | $2.0 \times 10^{-3}$ | S1 SLA1.101 |
| pSRQ2202 | Sc MS04 | S1 ML-3/2.201 | $3.0 \times 10^{-4}$ [d] | S1 ML-3/2.202 |
| Co-transfer pSRQ2201 and pSRQ2202 | S1 ML-3/2.202 | MS1 4/4.2 | $1.7 \times 10^{-8}$ | MS1 4/4.201 |
| | S1 ML-3/2.202 | Sld SLA3.25 | $2.0 \times 10^{-8}$ | Sld SLA3.2501 |

[a]Frequency is expressed as the number of Lac+ or MUC+ Lac+ Muc+ (co-transfer) transformants per donor CFR. Donor CFR were determined before mating. Frequency values reported are averages of at least two separate experiments.
[b]D-donor; R-recipient.
[c]Sc- *S. cremoris*; S1- *S. lactis*; MS1- malty *S. lactis*; Sld- *S. lactis* subsp. diacetilactis.
[d]Results from matings using phage lysate with titer $>1 \times 10^9$ PFU per ml.

The results of Example 1 presented clearly demonstrate that mucoid phenotype in the lactic streptococci examined is encoded on plasmid DNA. The association of mucoid phenotype with plasmid DNA in the wild type *S. cremois* MS was initially demonstrated by curing experiments. In these experiments, the presence or absence of 18.5 Mdalton plasmid correlated with mucoid and non-mucoid phenotypes respectively. The actual confirmation that mucoid phenotype is encoded on plasmid DNA was obtained in mating experiments, where the conjugative transfer of 18.5 Mdalton plasmid from mucoid *S. cremoris* MS04 to non-mucoid *S. lactis* ML-3/2.201 enabled the transconjugant containing the 18.5 Mdalton pSRQ2202 plasmid to express the mucoid phenotype. Additionally, the elimination of pSRQ2202 from the mucoid transconjugant *S. lactis* ML-3/2.202 resulted in a non-mucoid phenotype. Subsequently, pSRQ2202 was conjugatively transferred to *S. lactis* subsp. *diacetylactis* SLA 3.25 *S. lactis* 4/4.2. The phenotypic expression of pSRQ2202 in the respective transconjugants (*S. lactis* 4/4.201 and SLA 3.2501) indicate that in general, mucoid phenotype in lactic streptococci is linked to plasmid DNA.

The ease with which the Muc-plasmid was eliminated by incubating between 38° C. and 42° C. was in keeping with the earlier observation that to retain the desired mucoid characteristic in Scandinavian ropy milks, low temperature incubation between 13° C. to 18° C. is favored; incubation at temperatures higher than 27° C. to 30° C. resulted in considerable reduction or loss of desirable high viscosity and mucoidness.

In addition to the Muc-plasmid, transfer of Lac-plasmid was acheived. The Lac-plasmid from the wild-type mucoid *S. cremois* MS was first transferred to *Streptococcus lactis* ML-3/2.2 and subsequently the same plasmid was retransferred from *Streptococcus lactis* ML-3/2.201 to the Lac−, Muc+ derivative of the wild type mucoid *Streptococcus cremoris* (*S. cremois* MS04). Further, the plasmid was transferred from the Lac+ Muc+ transconjugant *S. lactis* ML-3/2.202 to the malty *S. lactis* 4/4.2 and *S. lactis* subsp. *diacetylactis* SLA 3.25. In the latter two matings, the Lac-plasmid also mobilized the Muc-plasmid and other cryptic plasmids. In all these transfers, the Lac+ phenotype was expressed in the respective transconjugants and the elimination of 75.8 Mdalton plasmid from the respective transconjugants rendered them Lac−.

Although the transfer of Muc-plasmid was detected in these mating experiments using indirect selection procedures, namely, scoring for Lac+ phenotype and/or phage-resistance, direct selection procedure through the use of other differential medium to distinguish between mucoid and non-mucoid colony types is possible. All of this is well known to those skilled in the art.

A significant finding in Example 1 was the association of phage resistance and mucoidness. With the transfer of Muc-plasmid to a non-mucoid, phage-sensitive recipient, the resultant mucoid transconjugant became resistant to the phage. This held true with *Streptococcus lactis* and *Streptococcus lactis* subsp. *diacetylactis*. The association of phage-resistance with mucoid phenotype in transconjugants offers another mechanism whereby phage-resistant derivatives for starter cultures can be made. Additionally, the selection procedure for the distinction of transconjugants through the use of high titer lytic phage lysates provides a means for avoiding drug markers for selection. This is especially significant in deriving desired strains for food and feed fermentations. It was also found that even if the Muc+ plasmid was cured from the transconjugant by high temperature incubation, the resulting strains were phage resistant although they had lost the ability to produce the mucoid substance. It appeared that at least a portion of the plasmid integrated with chromosomal material or with another part of the cell. This is a desirable method for fixing phage resistance into the bacterial cells.

Example 2

A well known non-mucoid commercial strain *Streptococcus cremoris* TR was rendered mucoid by transferring Muc+ phenotype from Lac− derivative of mucoid *Streptococcus lactis* transconjugant ML-3/2.202. Phage tr which is lytic for *S. cremois* TR was used to select against non-mucoid, phage-sensitive, Lac+ recipient cells. Only Lac+ survivor colonies from mating plates were picked into milk and tested for mucoidness. Mucoid cultures were purified on MIA and reexamined for mucoidness in milk, phage resistance, arginine hydrolysis, and subjected to plasmid analysis.

Mucoid transconjugant TR01 was resistant to phage tr, did not hydrolyize arginine and was Lac+.

Transconjugant TR01 was cured to Muc⁻ phenotype by high temperature incubation. The non-mucoid derivative retained resistance to phage tr.

The mucoid transconjugant and its non-mucoid cured derivative have no antibiotic markers and are suitable for food fermentations. If the bacteria are to be used in foods, selection is made for strains which are antibiotic sensitive.

Example 3

Muc-plasmid from Lac-cured derivative of *Streptococcus lactis* ML-3/2.202 was transferred to non-mucoid, Lac+, phage-sensitive *Streptococcus lactis* subsp. *diacetylactis* 18-16 using phage 18-16 as selecting agent. Only Lac+ colonies were selected to examine for mucoidness. Mucoid cultures were purified and reexamined for mucoidness, phage-resistance and subjected to confirmatory King's test.

Transconjugant *Streptococcus lactis* subsp. *diacetylactis* 18-16.01 does not have any antibiotic markers, and was Lac+, positive for diacetyl-acetoin production in milk resistant to phage 18-16, and mucoid. Comparison of plasmid profiles of parent *Streptococcus lactis* subsp. *diacetylactis* 18-16, transconjugant *Streptococcus lactis* subsp. *diacertylactis* 18-16.01 and donor Lac-cured *Streptococcus lactis* ML-3/2.202 showed that the mucoid transconjugant had acquired a 25 Mdalton plasmid, which coded for Muc+ phenotype. Apparently the 18.5 Mdal plasmid acquired some additional DNA through a recombinational event. The association of Muc+ phenotype with 25 Mdal plasmid was confirmed by curing studies.

The application of the mucoid *Streptococcus lactis* subsp. *diacetylactis* 18-16.01 transconjugant in Cottage cheese cream dressing was examined. Dry Cottage cheese curd is mixed with sufficient cream dressing to obtain stipulated milk fat content to meet legal specifications. The cream dressing may be cultured to develop diacetyl flavor and may contain hydrocolloid stabilizers (e.g., agar, carageenan, gums, and the like) to increase the viscosity of cream dressing so that it will adhere to cured surface rather than settling down to the bottom of the container. The use of flavor cultures in Cottage cheese dressing to develop diacetyl flavor and to increase shelf-life is well known in the industry. The use of the phage resistant, mucoid producing *Streptococcus lactis* subspecies *diacetylactis* in Cottage cheese creaming mixtures or other milk containing products to replace stabilizers is unknown. There are many naturally mucoid producing strains.

The use of mucoid *Streptococcus lactis* subsp. *diacetylactis* 18-16.01 in Cottage cheese dressing was examined for the following:

1. If half-and-half cream (18% milk fat) cultured with *Streptococcus lactis* subsp. *diacetylactis* 18-16.01 (1% inoculum, 16 hr. at 74° F.) is comparable in viscosity to commercial, non-cultured, stabilized Cottage cheese dressing.

2. If half-and-half cream cultured with strain 18-16.01 has better flavor characteristics than uncultured commercial dressing.

3. If half-and-half cream cultured with strain 18-16.01 when used as dressing at a dry curd: dressing ratio of 64:36 exhibits the same level of adherence to curd as commercial, stabilized, uncultured dressing used at the same ratio.

4. If cheese curd dressed with cultured half-and-half cream using strain 18-16.01 had better flavor (diacetyl) and keeping quality than cheese dressed with uncultured, stabilized, commercial dressing (stored at 40° F.–45° F.).

Dry Cottage cheese curd and uncultured, commercial cream dressing containing stabilizer mixture consisting of guar gum, carageenan, and locust bean gum and fungal inhibitor potassium sorbate were obtained from a local supplier. Half-and-half cream containing no additives was purchased from a local supermarket.

Dry Cottage cheese curd was washed in lightly chlorinated ice water and drained to remove excess water. A portion of half-and-half cream was seamed (in freely flowing steam in a chamber) for 30 minutes, cooled to 74° F. and cultured with *Streptococcus lactis* subsp. *diacetylactis* 18-16.01 (1% inoculum from a milk culture) for 16 hours at 74° F. After incubation the cultured half-and-half cream was chilled in an ice-bath. A psychrotrophic culture of Pseudomonas fragi PFO, isolated from spoiled Cottage cheese was grown overnight at 76° F. in Trypticase soy broth. The broth culture was diluted in sterile dilution buffer to obtain $1 \times 10^6$ to $1 \times 10^7$ cells per milliliter. The experimental variables were set up in the following manner:

1. 330 g dry curd + 170 g commercial dressing.
2. 330 g dry curd + 170 g half-and-half cultured with *Streptococcus lactis* subsp. *diacetylactis* 18-16.01.
3. 330 g dry curd + 170 g half-and-half.
4. 330 g dry curd + 170 g commercial dressing + *Pseudomonas fragi* PFO cells to give about $1 \times 10^4$ cells per gram of curd.
5. 330 g dry curd + 170 g half-and-half + *Pseudomonas fragi* PFO at about $1 \times 10^4$ cells per gram of curd.
6. 330 g dry curd + 170 g half-and-half cultured with strain 18-16.01 plus strain PFO added at about $1 \times 10^4$ cell per gram of curd.

Before preparing the Cottage cheese samples, uncultured half-and-half, cultured half-and-half and commercial dressing were tested for viscosity using Zahn cup #2.

Dressed curd at 500 g portions prepared according to the experimental design were made up in duplicates and distributed into duplicate plastic cartons. Cross contamination was avoided in all the operations. All the ingredients were kept cold in an ice-bath during the various operations. Packaged cartons were transferred to a walk-in cooler that was controlled at 40° F. At weekly intervals, one set of cartons representing the experimental variables were examined visually for spoilage and by smelling for development of diacetyl flavor or the lack or loss of developed diacetyl flavor, and for off-flavors. At the end of four-week period the duplicate, unopened set of cartons representing the experimental variables were checked and the results were recorded.

Results:
Viscosity Measurements:
Uncultured half-and-half = less than 100 centipoises
Stabilized commercial dressing = 150 centipoises
Half-and-half containing no stabilizer and cultured with Strain 18-16.01 = 180 centipoises

| | Storage studies: Storage at 40° F. | | | |
|---|---|---|---|---|
| Experimental | 1 week | 2 weeks | 3 weeks | 4 weeks |
| 1 | No flavor No spoilage | No flavor No spoilage | Spoiled | Spoiled |
| 2 | High flavor No spoilage | Good flavor No spoilage | Flat, no flavor Acid, no spoilage | Acid, Flat No spoilage |
| 3 | No flavor No spoilage | Partly spoiled (fruity) | Spoiled Completely | Badly spoiled |
| 4 | No flavor No spoilage | No flavor No spoilage | No flavor No spoilage | Flat spoiled |
| 5 | Spoiled | Spoiled | Spoiled | Spoiled |
| 6 | Slight flavor, No spoilage | Good flavor No spoilage | Flat, no flavor Acid, no spoilage | Slight rancid off-flavor, not spoiled |

The results showed that culturing with Strain 18-16.01 protected the cheese from psychrotrophic spoilage (variable 5 versus variable 6). Culturing with strain 18-16.01 also enhanced flavor (variable 1 and 4 versus variables 2 and 6). Comparable protection against spoilage by *P. fragi* PFO between variables 4 and 6 may be attributed to the presence of potassium sorbate in the commercial dressing. The cultured half-and-half did not contain any sorbate and the entire inhibitory activity was due to *S. lactis* subsp. *diacetylactis*.

The unopened cartons examined after 4 weeks showed similar results to the set examined at weekly intervals.

The cultured half-and-half had as good a viscosity and curd adhering property as stabilized, uncultured commercial creaming mixture. The use of mucoid *S. lactis* subsp. *diacetylactis* 18-16.01 eliminates the addition of stabilizers in the creaming mixture. Additionally, it provides good diacetyl flavor and increased shelf-life.

The stains can also be used in Cottage cheese containing fruits or fruit puree. The mucoidness can form a barrier around the curd and keep it separate from any fruit used in the Cottage cheese and prevent moisture loss from the curd due to osmotic pressure differential between the fruit and cheese curd.

Recently, a patent (Vedamuthu, E. R., et al., U.S. Pat. No. 4,382,097 (1983)), was issued for the application of ropy strains of *Streptococcus lactis* and/or *Streptococcus cremoris* in combination with non-mucoid cultures in specific proportions, for the production of non-ropy cultured dairy products possessing good viscosity and heavy body. Commercial concentrated cultures containing ropy and non-ropy lactic streptococci for the production of Cultured Buttermilk and Sour Cream are currently available in the United States. Such combination cultures help to maintain thick, heavy body in fermented dairy products without the use of hydrocolloid stabilizers or fortification with milk solids. The phage resistant and mucoid substance producing strains of the present invention can be used in these mixed cultures.

It will be appreciated that the 18.5 Mdal plasmid can be introduced into the sensitive strain by transformation of transduction or by bacterial conjugation. These techniques are well known to those skilled in the art.

I claim:

1. A method of increasing the thickness of milk products without addition of stabilizers which comprises:
    (a) providing in a milk containing product a *Streptococcus lactis* or *Streptococcus lactis* subspecies *diacetylactis* transconjugant harboring plasmid containing DNA isolated from an 18.5 Mdal parental plasmid referred to as PSRQ 2202 which encodes for production of a mucoid substance from *Streptococcus cremoris* (MS) NRRL-B-15995; and
    (b) incubating the milk containing product with the *Streptococcus lactis* or *Streptococcus lactis* subspecies *diacetylactis* transconjugant to develop a mucoid substance and to increases the thickness of the milk containing product.

2. The method of claim 1 in which the transconjugant is selected from *Streptococcus lactis* NRRL-B-15996 and *Streptococcus lactis* subsp. *diacetylactis* NRRL-B-15994 and NRRL-B-15997.

3. The method of claim 1 wherein the milk containing product is a Cottage cheese creaming mixture.

* * * * *

UNITED STATES PATENT AND TRADEMARK OFFICE
CERTIFICATE OF CORRECTION

PATENT NO. : 4,874,616

DATED : October 17, 1989

INVENTOR(S) : Ebenezer R. Vedamuthu

It is certified that error appears in the above—identified patent and that said Letters Patent is hereby corrected as shown below:

Face page under "References Cited", the following cited reference should be added --3,420,742, 1969, Farr--.

Column 2, line 38 "electrophoreis" should be --electrophoresis--.

Column 2, line 43 "MS01 (c)" should be --MS01 (C)--.

Column 2, lines 47 and 48 "cremois" should be --cremoris-- (three occurrences).

Column 3, line 10 "reistant" should be --resistant--.

Column 5, line 7 "4.7, 3.9, 2.7, 1.5" should be --4.7, 3.0, 2.7, 1.5--.

Column 5, line 48 "[a]Fus - Fusicid" should be --[a]Fus - Fusidic--.

Column 7, line 3 "whey-glucosse" should be --whey glucose--.

UNITED STATES PATENT AND TRADEMARK OFFICE
CERTIFICATE OF CORRECTION

PATENT NO. : 4,874,616

DATED : October 17, 1989

INVENTOR(S) : Ebenezer R. Vedamuthu

It is certified that error appears in the above—identified patent and that said Letters Patent is hereby corrected as shown below:

Column 7, line 24 "cremois" should be --cremoris--.

Column 9, line 3 "MUC+" should be --Muc$^+$--.

Column 9, line 64 "M-3/2.201" should be --ML-3/2.201--.

Column 10, line 57 "M-3/2.201" should be --ML-3/2.201--.

Column 10, line 59 "isolated" should be --isolates--.

Column 10, lines 66 and 67 "M-3/2.202" should be --ML-3/2.201--.

Column 11, line 1 "M-3/2.202" should be --ML-3/2.202--.

Column 11, line 3 "M-3/2.201" should be --ML-3/2.201--.

Column 11, line 6 "M-" should be --ML- --.

Column 11, line 12 "M-3/2.201" should be --ML-3/2.201--.

Column 11, lines 19, 20 and 21 "M-3/2.201" should be --ML-3/2.201-- (both occurrences).

Column 11, line 64 "Muc$^-$ Sm$^4$)" should be --Muc$^-$ Sm$^r$)--.

UNITED STATES PATENT AND TRADEMARK OFFICE
CERTIFICATE OF CORRECTION

PATENT NO. : 4,874,616
DATED : October 17, 1989
INVENTOR(S) : Ebenezer R. Vedamuthu It is certified that error appears in the above—identified patent and that said Letters Patent is hereby corrected as shown below:

Column 12, line 11 "M-3/2.202 should be --ML-3/2.202--.

Column 12, line 19 "M-3/2.202" should be --ML-3/2.202--.

Column 12, line 29 "beta-gycerophosphate" should be --beta-glycerophosphate--.

Column 12, line 42 "M-3/2.202" should be --ML-3/2.202--.

Column 13, line 1 "SA3.25" should be --SLA3.25--.

Column 13, Footnote "a" of Table 2, "MUC$^+$" should read --Muc$^+$ or--.

Column 13, line 30 "cremois" should be --cremoris--.

Column 13, line 59 "cremois" should be --cremoris--.

Column 13, line 63 "cremois" should be --cremoris--.

Column 14, line 60 "cremois" should be --cremoris--.

Column 14, line 68 "hydrolyize" should be --hydrolyze--.

Column 15, line 27 "diacertylactis" should be --diacetylactis--.

Column 16, line 17 "seamed" should be --steamed--.

UNITED STATES PATENT AND TRADEMARK OFFICE
CERTIFICATE OF CORRECTION

PATENT NO. : 4,874,616

DATED : October 17, 1989

INVENTOR(S) : Ebenezer R. Vedamuthu

It is certified that error appears in the above-identified patent and that said Letters Patent is hereby corrected as shown below:

Column 17, line 37, "stains" should be --strains--.

Column 18, line 42, "increases" should be --increase--.

Signed and Sealed this

Fifth Day of March, 1991

Attest:

HARRY F. MANBECK, JR.

*Attesting Officer*   *Commissioner of Patents and Trademarks*